US009760962B2

(12) United States Patent
Lese

(10) Patent No.: US 9,760,962 B2
(45) Date of Patent: Sep. 12, 2017

(54) ELECTRONIC HEALTH RECORD WEB-BASED PLATFORM

(75) Inventor: Gail B. Lese, Nahant, MA (US)

(73) Assignee: Everything Success IP LLC, Nahant, MA (US)

( * ) Notice: Subject to any disclaimer, the term of this patent is extended or adjusted under 35 U.S.C. 154(b) by 732 days.

(21) Appl. No.: 13/316,778

(22) Filed: Dec. 12, 2011

(65) Prior Publication Data

US 2012/0150564 A1 Jun. 14, 2012

Related U.S. Application Data

(60) Provisional application No. 61/421,816, filed on Dec. 10, 2010.

(51) Int. Cl.
*G06Q 50/22* (2012.01)
*G06Q 50/24* (2012.01)

(52) U.S. Cl.
CPC ......... *G06Q 50/24* (2013.01); *G06Q 2220/00* (2013.01)

(58) Field of Classification Search
CPC .............................. G06Q 50/22; G06Q 50/24
USPC ........................................................ 705/2–3
See application file for complete search history.

(56) References Cited

U.S. PATENT DOCUMENTS

| 6,327,570 | B1 | 12/2001 | Stevens |
| 6,574,606 | B1 | 6/2003 | Bell et al. |
| 6,604,681 | B1 | 8/2003 | Burke et al. |
| 7,174,302 | B2 | 2/2007 | Patricelli et al. |
| 7,640,271 | B2 * | 12/2009 | Logan, Jr. ............. G06F 19/322 |
| 8,266,441 | B2 * | 9/2012 | Inskeep ................ G06Q 20/341 713/185 |
| 8,275,635 | B2 | 9/2012 | Stivoric et al. |
| 8,341,714 | B2 * | 12/2012 | Muller et al. ..................... 726/9 |

(Continued)

FOREIGN PATENT DOCUMENTS

EP 1139200 A2 10/2001
FR EP 1933252 A1 * 6/2008 ............. G06F 21/34

(Continued)

OTHER PUBLICATIONS

Extended European Search Report for Application No. EP 11846295.1, mailed Jun. 29, 2016 ( 7 pages).

(Continued)

*Primary Examiner* — Eliza Lam
(74) *Attorney, Agent, or Firm* — Merchant & Gould P.C.

(57) ABSTRACT

A server for facilitating an electronic health record system. Each patient has a unique smart card. A processor: associates a security token with a patient; generates a one-time-use security code for storage based upon a security token; provides the one-time-use security code to the patient for storage on the smart card; applies two-factor authentication with the one-time-use security code for each login to a personal health record website presented by the processor; imports and exports the electronic health records associated with the patient based upon a request from the patient received through the personal health record website; generates a new one-time-use security code after each patient session based upon the respective security token; and provides the new one-time-use security code to the patient for storage on the smart card so that the personal health record website is accessed therewith.

20 Claims, 2 Drawing Sheets

(56) References Cited

U.S. PATENT DOCUMENTS

| | | |
|---|---|---|
| 2003/0121972 A1* | 7/2003 | Lee et al. ............... 235/380 |
| 2003/0158754 A1* | 8/2003 | Elkind ............ G06F 19/322 705/3 |
| 2005/0159984 A1* | 7/2005 | Hirano et al. ............... 705/3 |
| 2005/0165627 A1 | 7/2005 | Fotsch et al. |
| 2006/0190334 A1 | 8/2006 | Smith |
| 2006/0206361 A1 | 9/2006 | Logan, Jr. |
| 2007/0192137 A1 | 8/2007 | Ombrellaro |
| 2007/0255584 A1 | 11/2007 | Pavlatos et al. |
| 2007/0260511 A1 | 11/2007 | Bender, II |
| 2008/0289022 A1 | 11/2008 | Chiu |
| 2008/0300918 A1 | 12/2008 | Tenenbaum et al. |
| 2008/0319781 A1 | 12/2008 | Stivoric et al. |
| 2009/0019552 A1 | 1/2009 | McLaughlin et al. |
| 2009/0198618 A1* | 8/2009 | Chan ............ G06Q 20/02 705/66 |
| 2009/0222286 A1* | 9/2009 | Elsholz ............ G06F 19/322 705/3 |
| 2009/0300747 A1 | 12/2009 | Ahn |
| 2010/0030690 A1 | 2/2010 | Herlitz |
| 2010/0063845 A1 | 3/2010 | Yeluri et al. |
| 2010/0063846 A1 | 3/2010 | Shakamuri |
| 2010/0185461 A1 | 7/2010 | Broeska et al. |
| 2010/0235196 A1 | 9/2010 | Bartholomew, III et al. |
| 2010/0306858 A1 | 12/2010 | McLaren et al. |
| 2011/0119092 A1 | 5/2011 | Szela, Jr. et al. |
| 2011/0251854 A1 | 10/2011 | Chung |
| 2011/0295671 A1 | 12/2011 | Thomas et al. |
| 2014/0007205 A1* | 1/2014 | Oikonomou ............ G06F 21/35 726/6 |

FOREIGN PATENT DOCUMENTS

| | | |
|---|---|---|
| WO | WO 01/06468 A1 | 1/2001 |
| WO | WO-2005/036363 | 4/2005 |

OTHER PUBLICATIONS

Search Report and Written Opinion mailed Aug. 7, 2012, directed to International Application No. PCT/US2011/064363; 9 pages.

* cited by examiner

ELECTRONIC HEALTH RECORD WEB-BASED PLATFORM

CROSS-REFERENCE TO RELATED APPLICATION

This application claims priority to U.S. Provisional Patent Application No. 61/421,816 filed Dec. 10, 2010, which is incorporated herein by reference.

BACKGROUND OF THE INVENTION

1. Field of the Invention

The subject disclosure relates to methods and systems for storing and accessing electronic health records via a distributed computing network, and more particularly to improved methods and systems for allowing consumers to have control over and portability of their personal health information.

2. Background of the Related Art

Currently, a person's health information is distributed amongst each service provider. Thus, a person's doctor from 10 years ago may have certain information valuable to the current caregiver, but due to a lack of portability or ownership by the patient, such information is unavailable or difficult to obtain in a timely manner. As the world continues to spread the information revolution, access to vast informational resources and support systems becomes ubiquitous. Sitting in the glow of a computer screen, an individual can instantaneously access information on the opposite side of the planet.

SUMMARY OF THE INVENTION

As computing and interconnected communication capabilities continue to integrate into the daily activities of individuals, there is a need for a new and useful electronic medical record system that leverages new technologies.

In view of the above, a need exists for an electronic medical record system that quickly and easily provides patients with their full medical history in such a manner that the patient owns the information and can distribute the information in a timely manner. Preferably, the system is an open platform so that information can be leveraged by patients and providers equally.

The present disclosure is directed to a server for facilitating an electronic health record system that stores electronic health records related to a plurality of patients. Each patient has a unique smart card. A processor: associates a security token with a patient; generates a one-time-use security code for storage based upon a security token; provides the one-time-use security code to the patient for storage on the smart card; applies two-factor authentication with the one-time-use security code for each login to a personal health record website presented by the processor; imports and exports the electronic health records associated with the patient based upon a request from the patient received through the personal health record website; generates a new one-time-use security code after each patient session based upon the respective security token; and provides the new one-time-use security code to the patient for storage on the smart card so that the personal health record website is accessed therewith.

Preferably, a client communicates in a network in the electronic health record system and is selected from the group consisting of a personal computer, a computer workstation, a laptop computer, a server computer, a mainframe computer, a handheld tablet computer, a personal digital assistant, a cellular telephone, and combinations thereof. The unique smart card can include emergency contact information for the respective patient. The patients may be people, animals, and legal entities such as corporations, partnerships, and non-profit organizations. Proxy requests for the patient from a caregiver can provide the caregiver with access similar or the same as the patient. The processor may also populate a patient's medical profile data using data received from multiple sources including the patient and a caregiver of the patient. The smart card can also be tied to a royalty rewards program based on points that can be redeemed for related merchandise to provide incentive for participation.

It should be appreciated that the subject technology can be implemented and utilized in numerous ways, including without limitation as a process, an apparatus, a system, a device, a method for applications now known and later developed or a computer readable medium. These and other unique features of the system disclosed herein will become more readily apparent from the following description and the accompanying drawings.

BRIEF DESCRIPTION OF THE DRAWINGS

So that those having ordinary skill in the art to which the disclosed system appertains will more readily understand how to make and use the same, reference may be had to the following drawings.

DETAILED DESCRIPTION OF PREFERRED EMBODIMENTS

Figure 1:
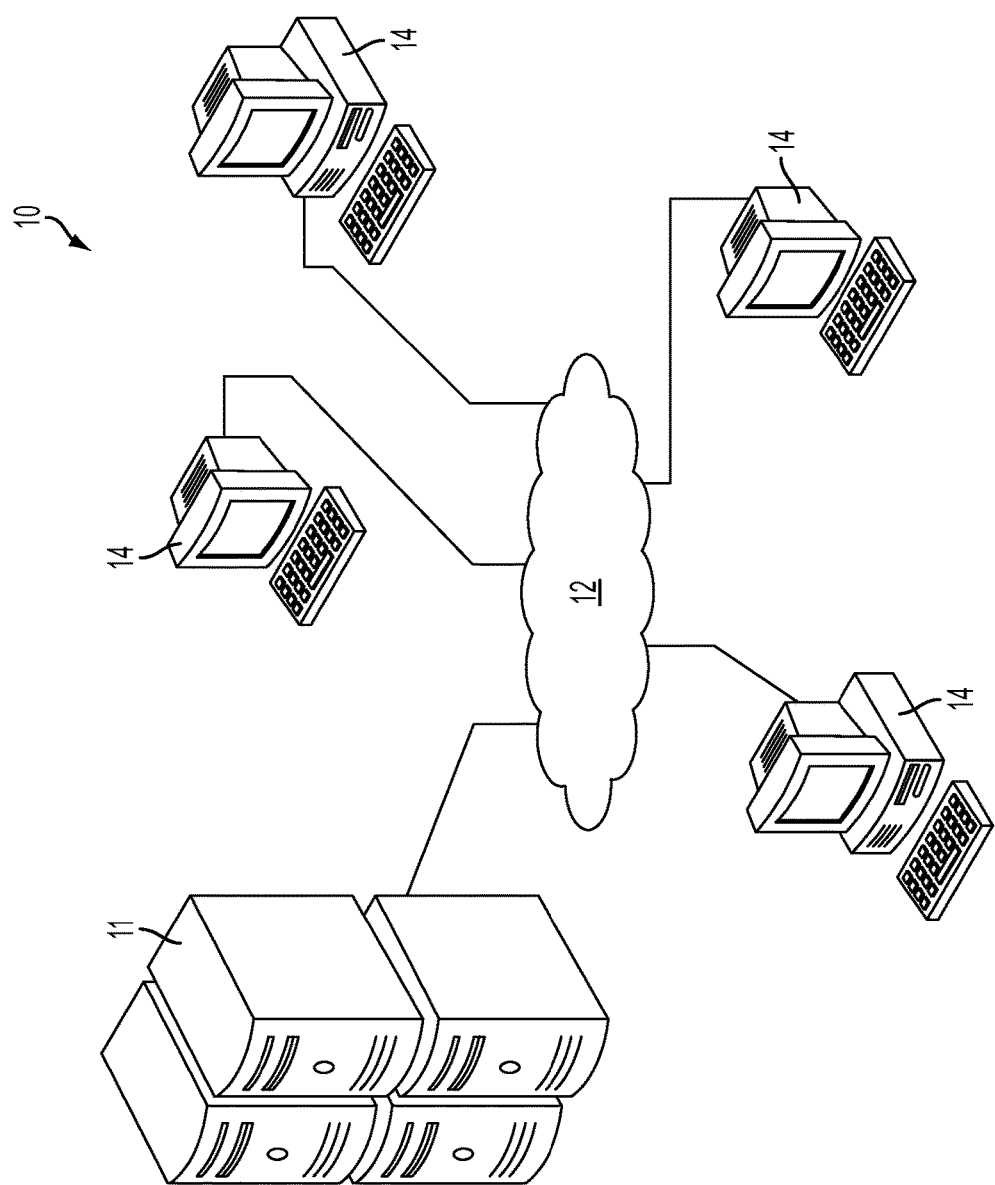
FIG. 1 is a diagram showing an environment having an electronic health record system in accordance with the subject disclosure.

The subject technology overcomes many of the prior art problems associated with electronic health records. The advantages, and other features of the system disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Referring now to the FIG. 1, an overview of an environment 10 for the electronic health record system embodying and implementing the methodology of the present disclosure is shown. The electronic health record system provides patients with secure access to personal electronic health information anywhere (web/Internet) including, but not limited to: personal computers, iPhones, Blackberries, Android phones, personal mobile devices and any Internet or communication network accessible devices worldwide. The following discussion describes the structure of such an environment 10 but further discussion of the applications program and data modules that embody the methodology of the present invention is described elsewhere herein and an infinite number of variations of each is contemplated.

The environment 10 includes one or more servers 11 which communicate with a distributed computer network 12 via communication channels, whether wired or wireless, as is well known to those of ordinary skill in the pertinent art. In the preferred embodiment, the distributed computer network 12 is the Internet or a private intranet. For simplicity, the following description refers to a single server 11 although several that function as a unit are shown. Server 11 hosts multiple Web sites and houses multiple databases necessary for the proper operation of the electronic health record system in accordance with the subject technology.

The server 11 is any of a number of servers known to those skilled in the art that are intended to be operably connected to a network so as to operably link to a plurality of clients 14 via the distributed computer network 12. As illustration, the server 11 typically includes a central processing unit including one or more microprocessors such as those manufactured by Intel or AMD, random access memory (RAM), mechanisms and structures for performing I/O operations, a storage medium such as a magnetic hard disk drive(s), and an operating system for execution on the central processing unit. The hard disk drive of the server 11 may be used for storing data, client applications and the like utilized by client applications. The hard disk drive(s) of the server 11 also are typically provided for purposes of booting and storing the operating system, other applications or systems that are to be executed on the server 11, paging and swapping between the hard disk and the RAM. It is envisioned that the server 11 can utilize multiple servers in cooperation to facilitate greater performance and stability of the subject invention by distributing memory and processing as is well known.

Distributed computer network 12 may include any number of network systems well known to those skilled in the art. For example, distributed computer network 12 may be a combination of local area networks (LAN), wide area networks (WAN), or, as is well known, the Internet. For the Internet, the preferred method of accessing information is the World Wide Web because navigation is intuitive and does not require technical knowledge.

The environment 10 also includes a plurality of computers or clients 14 such as desktop computers, laptop computers, personal digital assistants, tablets, cellular telephones and the like. The clients 14 allow users to access information on the server 11. For simplicity, only four clients 14 are shown. The clients 14 have displays and an input device(s) as would be appreciated by those of ordinary skill in the pertinent art (as would the server 11). The display may be any of a number of devices known to those skilled in the art for displaying images responsive to outputs signals from the computers 14. Such devices include but are not limited to cathode ray tubes (CRT), liquid crystal displays (LCDS), plasma screens and the like. Although a simplified diagram is illustrated in FIG. 1, such illustration shall not be construed as limiting the present invention to the illustrated embodiment. It should be recognized that the signals being outputted from the computer can originate from any of a number of devices including PCI or AGP video boards or cards mounted within the housing of the clients 14 that are operably coupled to the microprocessors and the displays of the clients 14.

Clients 14 typically provide consumer access to the environment. A plurality of users typically can share the same client 14 and cookie technology can be utilized to facilitate access to the environment 10. A plurality of users can utilize the environment 10 simultaneously. The clients 14 are also preferably equipped with an input device(s) as is known to those skilled in the art which can be used to provide input signals for control of applications programs and other programs such as the operating system being executed on the clients 14. In illustrative embodiments, the input device preferably comprises a switch, a slide, a mouse, a track ball, a glide point or a joystick, a microphone or other such device (e.g., a keyboard having an integrally mounted glide point or mouse) by which a user such as a consumer can input control signals and other commands. Any device is acceptable that generates the control signals or commands for implementing and interacting with the electronic health record system and the applications program embodying such methodology can be implemented in the form of discrete commands via a keyboard.

The clients 14 also typically include a central processing unit including one or more micro-processors such as those manufactured by Intel or AMD, random access memory (RAM), mechanisms and structures for performing I/O operations (not shown), a storage medium such as a magnetic hard disk drive(s), a device for reading from and/or writing to removable computer readable media and an operating system for execution on the central processing unit. According to one embodiment, the hard disk drive of the clients 14 is for purposes of booting and storing the operating system, other applications or systems that are to be executed on the computer, paging and swapping between the hard disk and the RAM and the like. In one embodiment, the application programs reside on the hard disk drive for performing the functions in accordance with the electronic health records system. In another embodiment, the hard disk drive simply has a browser for accessing an application hosted within the distributed computing network 12. The clients 14 can also utilize a removable computer readable medium such as a CD or DVD type of media that is inserted therein for reading and/or writing to the removable computer readable media.

Preferably, the graphical user interfaces (also referred to as "screens") used by the electronic health record system incorporate user-friendly features and fit seamlessly with other operating system interfaces, that is, in a framed form having borders, multiple folders, toolbars with pull-down menus, embedded links to other screens and various other selectable features associated with animated graphical representations of depressible buttons. These features can be selected (i.e., "clicked on") by the user via connected mouse, keyboard, voice command or other commonly used tool for indicating a preference in a computerized graphical interface Referring now to FIG. 2, there is illustrated a flowchart 100 depicting a process for providing patients with ownership of their electronic health records in accordance with an embodiment of the present technology. The flowchart 100 illustrates a structure or the logic of the present technology, possibly as embodied in computer program software for execution on a computer, digital processor or microprocessor. Those skilled in the art will appreciate that the flow chart illustrates the structures of the computer program code elements, which may include logic circuits on an integrated circuit, that function according to the present technology. As such, the present technology may be practiced by a machine component that renders the program code elements in a form that instructs a digital processing apparatus (e.g., a client computer and/or server) to perform a sequence of function step(s) corresponding to those shown in the flow charts.

In a preferred embodiment, a company, a country, an association, or the like (not shown) hosts a Web site using the environment 10 to provide access for the electronic health record system. Further, the environment provider may maintain banner advertisements and links to related Web sites as well as offer related products and services, whether or not co-branded, as a source of additional revenue. Preferably, the electronic health record system is established by a government in association with a national health plan by paying a fee to one or more technology, maintenance and service providers. In one embodiment, the government pays a fee for each user enrolled in the electronic medical record system. In another embodiment, the environment provider is an association of veterinary doctors and hospitals to provide the electronic health record system for pets and their owners. In one embodiment, banner advertisements and links are associated with national and local vendors of medical related goods and services and the company receives a further fee based upon referrals.

It is envisioned that the hosted electronic health record system provides for administration and security maintenance. At step S1 of the process 100, a user requests enrollment in the electronic health record system. In order to enroll, the personal information of the user is required. The personal information may be a social security number or related identifier issued to every citizen by a government entity, name, date of birth, address, telephone number as well as specific medical information such as health and pre-exiting conditions and like information.

At step S2, a security card 18 is provisioned and mailed to the enrolled users. The security card 18 includes a magnetic strip or other means to store information as well as holograms and other forgery prevention features now known and later developed. The security card 18 also lists emergency contact information for the user to be useful in the event of an emergency (information such as known allergies, conditions, and blood type) in addition to acting as a loyalty card for associated companies. The smart card 18 is also branded to enhance the likelihood of the patient seeking out and utilizing goods and services associated the brand. Indeed, usage of the card 18 may be tied to a royalty rewards program. The information on the security card 18 may be the same information noted above plus other information such as a security token and a one-time-use security code.

Figure 2:
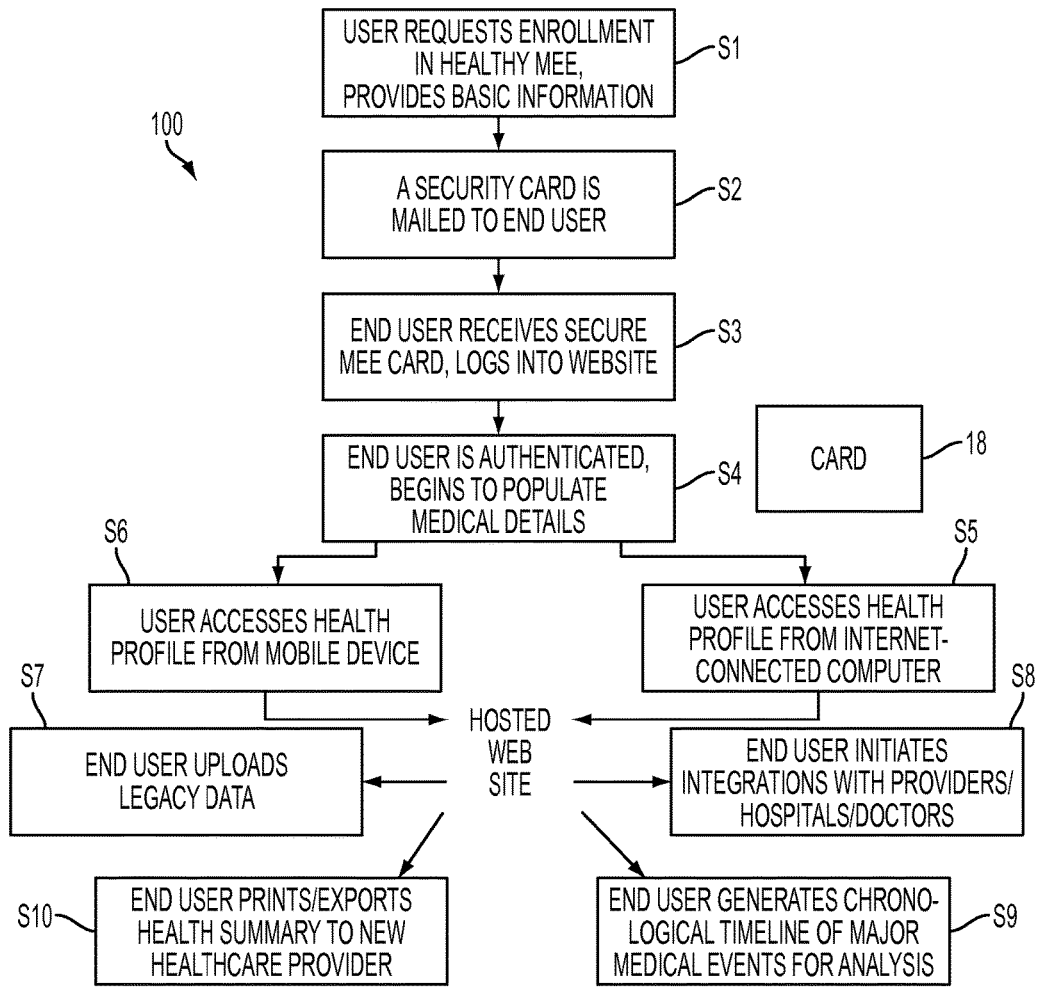
FIG. 2 is a flow diagram of a process performed by the electronic health record system of FIG. 2.

Still referring to FIG. 2, at step S3, the user has possession of the security card 18 and logs into the hosted Web site. Access to general portions of the Web site may not require authenticated access. However, in order for a user to access and modify their personal information, authentication is required as noted in step S4.

In one embodiment, the subject technology uses two-factor authentication with the security token and one-time-use security code. Upon authentication, the electronic health record system provides another one-time-use code for the next login. Each one-time-use security code is stored on the smart card 18 by swiping the card through a read/write device associated with the client 14. The server 11 hosting the personal health record website creates a record associated the one-time-use security codes with the respective users.

As can be seen at steps S5 and S6, the user may access their health profile through the hosted Web site by using an Internet connected computer or a mobile device.

The electronic health record system not only allows provisioning of an individual login for each user to access his or her personal electronic health data but also supports individual-owned data. Thus, a user may import and export data freely provided proper authentication occurs. By having the user own their respective health profile, the user can easily provide such information to caregivers, insurance companies, the Internal Revenue Service and the like.

At step S7, the user uploads legacy data in their profile. The profile information is uploaded to the application either by the individual via manual data entry, or by a variety of back-end healthcare provider integrations associated with physicians, specialists, pharmacists, veterinarians and the like. All information gathered can be freely exported by the individual user. The individual must have the security card 18 in their possession in order to provide/obtain the security token and the one-time-use security code to gain access to the site. As noted above, a new code is generated on the smart card 18 for each time the user logs into the secure website. The application allows the uploading of patient lab/test results, photos, diagnostic images, paper records and other electronic documents/files.

The electronic health record system contains data that is user owned and provider agnostic. Particular providers, platforms, and electronic health applications are not favored over others. At step S8, the user initiates integration with provider, hospitals and doctors so that all platforms, providers, and existing electronic health applications are supported and information can be passed from multiple sources to the user's online record.

If a caregiver desires access to the user's electronic health record, the user can provide the caregiver with proxy access or download and provide the desired information. For example, as shown in step S9, the user generates a chronological timeline of major medical events for analysis. For another example, as shown in step S10, the user exports or prints a health summary to a new healthcare provider. Such caregivers may pay a subscription fee to the entity hosting the electronic medical record system. As a benefit, the caregivers need for data retention and technology supporting the same is alleviated. Further, as users switch between caregivers, by having user control and ownership of the information, lost or incomplete data histories are reduced if not eliminated.

The caregivers can also further benefit from having additional goods and services paired with health plan benefits. For example, employees enrolled in a dental plan for a monthly fee can receive points for usage, participation and performance. The points could be redeemed at merchants or with the entity hosting the electronic health record system for related and unrelated merchandise to provide incentive for participation.

The electronic health record system may also cross-sell products via the hosted web site and other advertising such as co-branded marketing. An example of a system utilizing the Internet for cross-selling is U.S. Pat. No. 6,604,681 to Burke et al., which is incorporated herein by reference. Burke et al. disclose a shopping assistant system designed to provide consumers with information about a product of interest. The consumer uses a portable device to receive the desired information based on information associated with the user. The subject technology can utilize these same cross-selling techniques at a desirable cost. Still another example of applicable technology is U.S. Pat. No. 6,574,606 to Bell et al. which is incorporated herein by reference. Bell et al. provide a method for cross-marketing products by providing hyperlinks to a related merchant's Web site from a vendor's Web site. The vendor Web site also uses artwork to identify the Web site as associated with the vendor and banner advertisements for presenting offers.

It will be appreciated by those of ordinary skill in the pertinent art that the functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, databases, interfaces, computers, servers and the like) shown as distinct for purposes of illustration may be incorporated within other functional elements in a particular implementation.

For example, the subject technology can be beneficially used in the United States, Europe, Eurasia, in Gulf Coast States such as the United Arab Emirates and Saudi Arabia, among other countries in the world. The subject technology has wide application to various fields such as dentistry, animal related health information, personal credit history information and so on. For example in a credit history application, certain specified bureaus or entities could have similar or even the same access level as the users to update a credit record based upon relevant activity. Such bureau updates would not be subject to change by the user associated therewith out prior acceptance through, for example, an administrative appeal process.

To access the technology, a secure log on alone can be used or with any additional applications to the security that tie into various technology such as the web, platforms accessible from anywhere, and the like now known and later developed.

The subject technology also includes, but is not limited to a three in one embodiment of: secure log in card for electronic medical records; loyalty card redeemed against product or services and also with offers tailored to the buying habits of each individual customer; and/or insurance by which customers pay a premium and are covered to agreed limits for all necessary treatments and health care, on a contributory basis (the policy pays an agreed percentage of the total cost) and/or a Membership Scheme/plan by which customers choose an appropriate schedule of treatments, and pay monthly.

While the invention has been described with respect to preferred embodiments, those skilled in the art will readily appreciate that various changes and/or modifications can be made to the invention without departing from the spirit or scope of the invention. In particular, each of the claims can be combined in any manner as well as included in part and whole with other information described herein to create a large number of variations of application of the subject technology.

What is claimed is:

1. An electronic health record system for providing secure patient management of electronic health records, the system comprising:
   a smart card associated with a first patient of a plurality of patients, the smart card being configured to store a security token and a one-time-use security code thereon for use in securely accessing an electronic health record associated with the first patient and, upon an end of a patient session on a personal health record website, replace the one-time use security code with a new one-time-use security code;
   a server configured to communicate with a client via a distributed computing network, thereby providing the first patient with a portal to access a personal health record website hosted by the server, the server including:
   (a) a memory storing an instruction set and electronic health records related to the plurality of patients; and
   (b) a processor for running the instruction set, the processor being in communication with the memory and the distributed computing network, wherein the processor is operative to:
   (i) associate the security token with the first patient;
   (ii) generate the one-time-use security code for storage based upon the security token;
   (iii) provide the one-time-use security code to the smart card of the first patient via a read/write device coupled to the client and configured to write information to the smart card;
   (iv) apply two-factor authentication with the one-time-use security code for each login to the personal health record website;
   (v) display to the first patient, via the client, the electronic health record associated with the first patient based upon a request from the first patient received through the personal health record web site;
   (vi) receive additional medical data relating to the first patient via the client;
   (vii) update the electronic health record associated with the first patient with the additional medical data relating to the first patient;
   (viii) generate the new one-time-use security code after each session on the personal health record website by the first patient based upon the security token; and
   (ix) provide the new one-time-use security code to the the smart card via the read/write device coupled to the client for storage onto the smart card to enable subsequent access to the personal health record website by the first patient using the smart card.

2. The system of claim 1, wherein the client is selected from the group consisting of a personal computer, a computer workstation, a laptop computer, a server computer, a mainframe computer, a handheld tablet computer, a personal digital assistant, a cellular telephone, and combinations thereof.

3. The system of claim 1, wherein the smart card is further configured to store emergency contact information for the first patient.

4. The system of claim 1, wherein the first patient is selected from the group consisting of a person, an animal, and a legal entity such as a corporation, a partnership, and a nonprofit organization.

5. The system of claim 1, wherein the request from the first patient is based on a proxy request for the first patient from a caregiver.

6. The system of claim 1, wherein the processor is further operative to populate the first patient's electronic health record with data received from multiple sources including the first patient and a caregiver of the first patient.

7. The system of claim 1, wherein the of client is a personal mobile device.

8. The system of claim 1, wherein the additional medical data relating to the first patient comprises legacy medical information provided by the first patient.

9. The system of claim 8, wherein the legacy medical information provided by the first patient includes at least one of diagnostic images, test results, lab results, and operative reports.

10. The system of claim 1, wherein a timeline of major medical events is generated according to the updated electronic health record comprising the additional medical data relating to the first patient.

11. The system of claim 1, wherein the processor is further operative to (i) receive a request from the first patient to export a health summary and (ii) generate the requested health summary for export.

12. The system of claim 11, wherein the health summary is generated from the updated electronic health record associated with the first patient.

13. An electronic health record system for providing secure patient management of electronic health records, the system comprising:

a mobile device;

a smart card associated with a first patient of a plurality of patients, the smart card being configured to store a security token and a one-time-use security code thereon for use in securely accessing an electronic health record associated with the first patient and, upon an end of a patient session on a personal health record website, replace the one-time use security code with a new one-time-use security code;

a database storing electronic health records related to the plurality of patients;

a server configured to communicate with the database and the mobile device via a distributed computing network, thereby providing the first patient with a portal to access a personal health record website hosted by the server, the server including:

(a) a memory storing an instruction set; and (b) a processor for running the instruction set, the processor being in communication with the memory and the distributed computing network, wherein the processor is operative to:

(i) associate the security token with the first patient;

(ii) generate the one-time-use security code for storage based upon the security token;

(iii) provide the one-time-use security code to the smart card of the first patient via a read/write device coupled to the mobile device and configured to write information to the smart card;

(iv) apply two-factor authentication with the one-time-use security code for each login to the personal health record website;

(v) display, on the mobile device, the electronic health record associated with the first patient based upon a request from the first patient received through the personal health record website;

(vi) generate the new one-time-use security code after each session on the personal health record website by the first patient based upon the security token; and (vii) provide the new one-time-use security code to the smart card via the read/write device coupled to the mobile device for storage onto the smart card to enable subsequent access to the personal health record website by the first patient using the smart card.

14. The system of claim 13, wherein the processor is further operative to (i) receive additional medical data relating to the first patient via the mobile device, and (ii) update the electronic health record associated with the first patient with the additional medical data relating to the first patient.

15. The system of claim 14, wherein the additional medical data relating to the first patient comprises legacy medical information provided by the first patient.

16. The system of claim 15, wherein the legacy medical information provided by the first patient includes at least one of diagnostic images, test results, lab results, and operative reports.

17. The system of claim 14, wherein a timeline of major medical events is generated according to the updated electronic health record comprising the additional medical data relating to the first patient.

18. The system of claim 14, wherein the processor is further operative to (i) receive a request from the first patient to export a health summary and (ii) generate the requested health summary for export.

19. The system of claim 1, wherein the processor is further operative to display, via the personal health record website, a timeline of a plurality of medical events relating to the first patient, the plurality of medical events based at least in part on the updated electronic health record associated with the first patient.

20. The system of claim 1, wherein the processor is further operative to receive a request from the first patient, via the personal health record website, to send the updated electronic health record associated with the first patient to a medical provider.

* * * * *